US010806273B2

(12) United States Patent
Nakamura et al.

(10) Patent No.: US 10,806,273 B2
(45) Date of Patent: Oct. 20, 2020

(54) MATTRESS

(71) Applicant: Sumitomo Riko Company Limited, Aichi (JP)

(72) Inventors: Yasuhiro Nakamura, Aichi (JP); Susumu Sato, Aichi (JP); Akitsugu Misaki, Aichi (JP); Tomonori Hayakawa, Aichi (JP)

(73) Assignee: SUMITOMO RIKO COMPANY LIMITED, Aichi (JP)

( * ) Notice: Subject to any disclaimer, the term of this patent is extended or adjusted under 35 U.S.C. 154(b) by 296 days.

(21) Appl. No.: 15/342,499

(22) Filed: Nov. 3, 2016

(65) Prior Publication Data

US 2017/0251823 A1 Sep. 7, 2017

(30) Foreign Application Priority Data

Mar. 2, 2016 (JP) ................................ 2016-040393

(51) Int. Cl.
*A47C 27/08* (2006.01)
*A47C 27/05* (2006.01)
(Continued)

(52) U.S. Cl.
CPC .......... *A47C 27/083* (2013.01); *A47C 27/001* (2013.01); *A47C 27/002* (2013.01);
(Continued)

(58) Field of Classification Search
CPC ............ A61G 2203/30; A61G 2203/34; A61G 7/05769; A61G 7/05715; A47C 27/083;
(Continued)

(56) References Cited

U.S. PATENT DOCUMENTS 7,652,581 B2 * 1/2010 Gentry ..................... A61B 5/11
340/573.1
8,852,095 B2 * 10/2014 Schlottau ............... A41D 1/002
2/171
(Continued)

FOREIGN PATENT DOCUMENTS

CN 103619217 A 3/2014
CN 15342499 A 11/2016
(Continued)

OTHER PUBLICATIONS

China Official Action received in 201710068637.8, dated Dec. 4, 2018.
(Continued)

*Primary Examiner* — Eric J Kurilla
*Assistant Examiner* — Amanda L Bailey
(74) *Attorney, Agent, or Firm* — Greenblum & Bernstein, P.L.C.

(57) ABSTRACT

A mattress including: a support surface to support a user; a mattress main body that constitutes the support surface; at least one pressure sensor having a flexible sheet shape to detect a pressure acting on the support surface; a support surface cover positioned with respect to the mattress main body and arranged so as to cover the support surface; and at least one positioning member provided to the support surface cover to permit a movement of the pressure sensor with respect to the support surface cover in a planar direction while limiting an amount of the movement of the pressure sensor with respect to the support surface cover in the planar direction such that the pressure sensor is positioned on the support surface by the positioning member.

11 Claims, 7 Drawing Sheets

(51) Int. Cl.
*A47C 27/00* (2006.01)
*A47C 27/10* (2006.01)
*A61G 7/057* (2006.01)

(52) U.S. Cl.
CPC .......... *A47C 27/056* (2013.01); *A47C 27/082* (2013.01); *A47C 27/10* (2013.01); *A61G 7/05769* (2013.01); *A61G 7/05715* (2013.01); *A61G 2203/34* (2013.01)

(58) Field of Classification Search
CPC ... A47C 27/001; A47C 27/002; A47C 27/056; A47C 27/082; A47C 27/10
See application file for complete search history.

(56) References Cited

U.S. PATENT DOCUMENTS

| | | | | |
|---|---|---|---|---|
| 2004/0111045 | A1* | 6/2004 | Sullivan .................. | A61B 5/11<br>600/595 |
| 2005/0190068 | A1* | 9/2005 | Gentry .................... | A61B 5/11<br>340/665 |
| 2011/0001622 | A1 | 1/2011 | Gentry et al. | |
| 2011/0308019 | A1* | 12/2011 | Terawaki ............ | A61B 5/6892<br>5/713 |
| 2012/0116251 | A1 | 5/2012 | Ben-Shalom et al. | |
| 2014/0130264 | A1* | 5/2014 | Misaki .................. | A47C 27/10<br>5/713 |
| 2016/0367171 | A1* | 12/2016 | Shimizu .............. | A61B 5/6892 |

FOREIGN PATENT DOCUMENTS

| | | | |
|---|---|---|---|
| JP | 2006-512112 | A | 4/2006 |
| JP | 2007-525266 | A | 9/2007 |
| JP | 2013-27532 | A | 2/2013 |
| WO | 2015186182 | A1 | 12/2015 |

OTHER PUBLICATIONS

Office Action issued in China Counterpart Patent Appl. No. 201710068637.8, dated Apr. 16, 2019, along with an English translation thereof.
Japanese Office Action dated Dec. 23, 2019 together with its English-language translation on the corresponding Japanese Patent Application No. 2016-040393.

* cited by examiner

MATTRESS

INCORPORATED BY REFERENCE

The disclosure of Japanese Patent Application No. 2016-040393 filed on Mar. 2, 2016 including the specification, drawings and abstract is incorporated herein by reference in its entirety.

BACKGROUND OF THE INVENTION

1. Field of the Invention

The present invention relates to a mattress spread on a bed or the like, for example, for supporting a user.

2. Description of the Related Art

Conventionally, there is known a mattress spread on a bed or the like, for example, for resting and supporting a user. The mattress generally includes a mattress main body having a structure in which a metal spring and a cushion made of urethane foam etc. are combined, or a structure in which a plurality of hollow cells are arranged and disposed, and so forth. The mattress is used for the purpose of dispersing a body pressure of the user so as to provide a good comfort of sleeping or the like.

Meanwhile, in order to obtain information about distributions of body pressures of the user acting on the support surface of the mattress main body or the like, proposed is a pressure sensor provided to the mattress. As disclosed in U.S. Publication No. US 2012/0116251, the pressure sensor is arranged on the support surface of the mattress main body, and is configured to detect the body pressure distribution, respiratory movement, or the like of the user by detecting a compression between the user and the support surface.

However, with the pressure sensor simply spread on the support surface of the mattress main body, when the user moves on the support surface, the pressure sensor may move in the planar direction relative to the support surface. Accordingly, there is a risk that the position where the pressure is detected by the pressure sensor and the position on the support surface where the pressure really acts may considerably deviate with respect to each other.

On the other hand, if the pressure sensor is fixed and firmly positioned with respect to the support surface, the amount of deformation of the mattress in response to input of the user's body pressure may be limited by the pressure sensor which generally has lower elasticity than that of the support surface or mattress cover. This may cause the troubles of deterioration in comfort of sleeping or the like.

SUMMARY OF THE INVENTION

It is therefore one object of this invention to provide a mattress of novel structure which is able to realize pressure detection by means of the pressure sensor with excellent accuracy while minimizing influence on deformation characteristics of the mattress due to arrangement of the pressure sensor.

The above and/or optional objects of this invention may be attained according to at least one of the following modes of the invention. The following modes and/or elements employed in each mode of the invention may be adopted at any possible optional combinations.

Specifically, a first mode of the present invention provides a mattress comprising: a support surface to support a user; a mattress main body that constitutes the support surface; at least one pressure sensor having a flexible sheet shape to detect a pressure acting on the support surface; a support surface cover positioned with respect to the mattress main body and arranged so as to cover the support surface; and at least one positioning member provided to the support surface cover to permit a movement of the pressure sensor with respect to the support surface cover in a planar direction while limiting an amount of the movement of the pressure sensor with respect to the support surface cover in the planar direction such that the pressure sensor is positioned on the support surface by the positioning member.

With the mattress constructed according to the first mode, the amount of the movement of the pressure sensor with respect to the support surface in the planar direction is limited by the positioning member. This will prevent the considerable deviation of the position where the pressure is detected by the pressure sensor with respect to the position on the support surface where the pressure really acts. Accordingly, the pressure acting on the support surface will be detected by the pressure sensor with high accuracy, thereby surely realizing mattress control for actively dispersing the body pressure, recognition of respiration of the user, or the like.

Moreover, the pressure sensor is positioned so as to be movable to some extent in the planar direction without being excessively restrained by the positioning member. Therefore, when the support surface cover undergoes flexural deformation due to action of the load, the pressure sensor, which is generally resistant to extension/contraction compared to the support surface cover, undergoes flexural deformation while deviating with respect to the support surface cover in the planar direction. This makes it possible to prevent the pressure sensor from limiting the amount of deformation of the support surface cover. Note that the relative deviation in the planar direction between the positions of the pressure sensor and the support surface generated during deformation of the support surface cover and the pressure sensor is sufficiently small to the extent such that influence on the pressure detection does not substantially pose any problems, and in preferred practice, such deviation is made smaller than the amount of movement of the pressure sensor in the planar direction permitted by the positioning member.

A second mode of the present invention provides the mattress according to the first mode wherein the support surface cover includes a bag-shaped pocket body that serves as the positioning member, and the pressure sensor is housed within the pocket body in a non-adhesive way so as to be positioned on the support surface.

According to the second mode, since the positioning member, which is arranged at the position closer to the user than the support surface, has a bag shape, it is easy to keep the contact face of the mattress flexible against the user, thereby providing a good comfort of sleeping to the user.

A third mode of the present invention provides the mattress according to the second mode wherein an opening and closing member is provided to open and close an opening part of the pocket body.

According to the third mode, by closing the opening part of the pocket body, which houses the pressure sensor, by means of the opening and closing member, it is possible to position the pressure sensor in a prescribed position in an appropriately disposed state of being housed within the pocket body. Also, by opening the opening part of the pocket body, it is possible to take the pressure sensor out of the pocket body, thereby readily exchanging the pressure sensors.

A fourth mode of the present invention provides the mattress according to the second or third mode wherein a retaining cushion is housed within the pocket body, and the retaining cushion is arranged between the support surface and the pressure sensor.

According to the fourth mode, the pressure sensor is elastically retained by the retaining cushion in a housed state within the pocket body. This will prevent the pressure sensor from moving or deforming any more than necessary within the internal space of the pocket body. Moreover, the elastic deformation of the retaining cushion will permit the pressure sensor housed within the internal space of the pocket body to undergo flexural deformation. Thus, support of the pressure sensor by the retaining cushion will not have an adverse effect on the followability to deformation of the support surface cover.

A fifth mode of the present invention provides the mattress according to any one of the first through fourth modes wherein the mattress main body includes a hollow-structured cell having a fluid chamber, the cell constitutes at least a portion of the support surface, and the cell is capable of extension/contraction due to supply and exhaust of a fluid with respect to the fluid chamber in the cell.

With the fifth mode, the support surface may be composed of a plurality of cells. Since the pressure sensor is positioned with respect to the support surface by means of the positioning member, by arranging a plurality of pressure detection parts on the pressure sensor, for example, it is possible to accurately detect the pressure acting on the corresponding cells.

A sixth mode of the present invention provides the mattress according to any one of the first through fifth modes wherein the at least one positioning member comprises a plurality of positioning members provided to the support surface cover, and the at least one pressure sensor comprises a plurality of pressure sensors such that the positioning members position the respective pressure sensors.

According to the sixth mode, by disposing the plurality of pressure sensors on the support surface, each pressure sensor can be made small, so that the deviation of the pressure sensor with respect to the support surface in the planar direction will decrease, as well as production of the pressure sensors will become easy.

A seventh mode of the present invention provides the mattress according to any one of the first through sixth modes wherein the positioning member is elastically deformable.

According to the seventh mode, the positioning member is permitted to undergo elastic deformation such as extensional and contractive deformation, flexural deformation, or the like. Therefore, deformation of the support surface cover is less likely to be limited by the positioning member, whereby the positioning member is less prone to have an adverse effect on the feel of the contact face with the user.

An eighth mode of the present invention provides the mattress according to any one of the first through seventh modes wherein the positioning member is provided to the support surface cover in an undetachable way, while the pressure sensor is removable from the positioning member.

According to the eighth mode, the positioning member is accurately positioned with respect to the support surface cover, thereby avoiding deviation of the pressure sensor with respect to the support surface due to deviation of the positioning member with respect to the support surface cover. Besides, since the positioning member or the pressure sensor will not accidentally be detached from the support surface cover, handling of the support surface cover becomes easy. Moreover, by removing the pressure sensor from the positioning member so as to detach it from the support surface cover, the support surface cover and the positioning member can be readily washed.

A ninth mode of the present invention provides the mattress according to any one of the first through seventh modes wherein the positioning member is detachable with respect to the support surface cover.

According to the ninth mode, in the case where the support surface cover gets soiled or damaged, the support surface cover can also be separately washed or exchanged. Also, in the case where the positioning member gets soiled or damaged, the positioning member can be detached from the support surface cover so as to be washed or exchanged. In addition, it would also be possible to change the attachment position of the positioning member with respect to the support surface cover depending on the physique of the user or the like.

A tenth mode of the present invention provides the mattress according to any one of the first through ninth modes wherein the pressure sensor comprises a capacitance type pressure sensor having a structure in which a plurality of pressure detection parts are arranged two dimensionally, each pressure detection part comprising electrodes placed in opposition and an insulative dielectric layer disposed between the electrodes, and the pressure sensor is configured to detect the pressure acting on the support surface based on an amount of change in electrostatic capacity of each pressure detection part generated by a change in distance between the electrodes when the pressure acts on the support surface.

According to the tenth mode, since the pressure sensor is positioned by the positioning member with respect to the support surface, the plurality of pressure detection parts arranged two dimensionally are each positioned in a prescribed position on the support surface, thereby accurately detecting the pressures acting on the support surface. In particular, in the case where at least a portion of the support surface is constituted by the cell, if the pressure detection part of the pressure sensor and the cell deviate relative to each other in the planar direction, there is a risk that the pressure detection precision may be considerably deteriorated. In this respect, since the pressure detection part is positioned with respect to the cell by the positioning member in the planar direction, it is possible to stably detect the pressure with desired accuracy.

According to the present invention, a positioning member is provided to the support surface cover that covers the support surface of the mattress main body, and the positioning member permits the movement of the pressure sensor having a flexible sheet shape with respect to the support surface cover in the planar direction while limiting the amount of the movement thereof. By so doing, the pressure sensor is positioned with respect to the support surface and is able to accurately detect the pressure acting on the support surface. Besides, the deformation of the support surface cover will sufficiently occur without being restrained by the pressure sensor, thereby providing a good comfort of sleeping to the user.

BRIEF DESCRIPTION OF THE DRAWINGS

The foregoing and/or other objects, features and advantages of the invention will become more apparent from the following description of a preferred embodiment with reference to the accompanying drawings in which like reference numerals designate like elements and wherein:

FIGS. 3A and 3B are views of a pressure sensor constituting the mattress shown in FIG. 1, wherein FIG. 3A shows a plan view of an assembled state of the pressure sensor and FIG. 3B shows a perspective view of an exploded state of the pressure sensor, respectively;

DETAILED DESCRIPTION OF PREFERRED EMBODIMENTS

Figure 1:
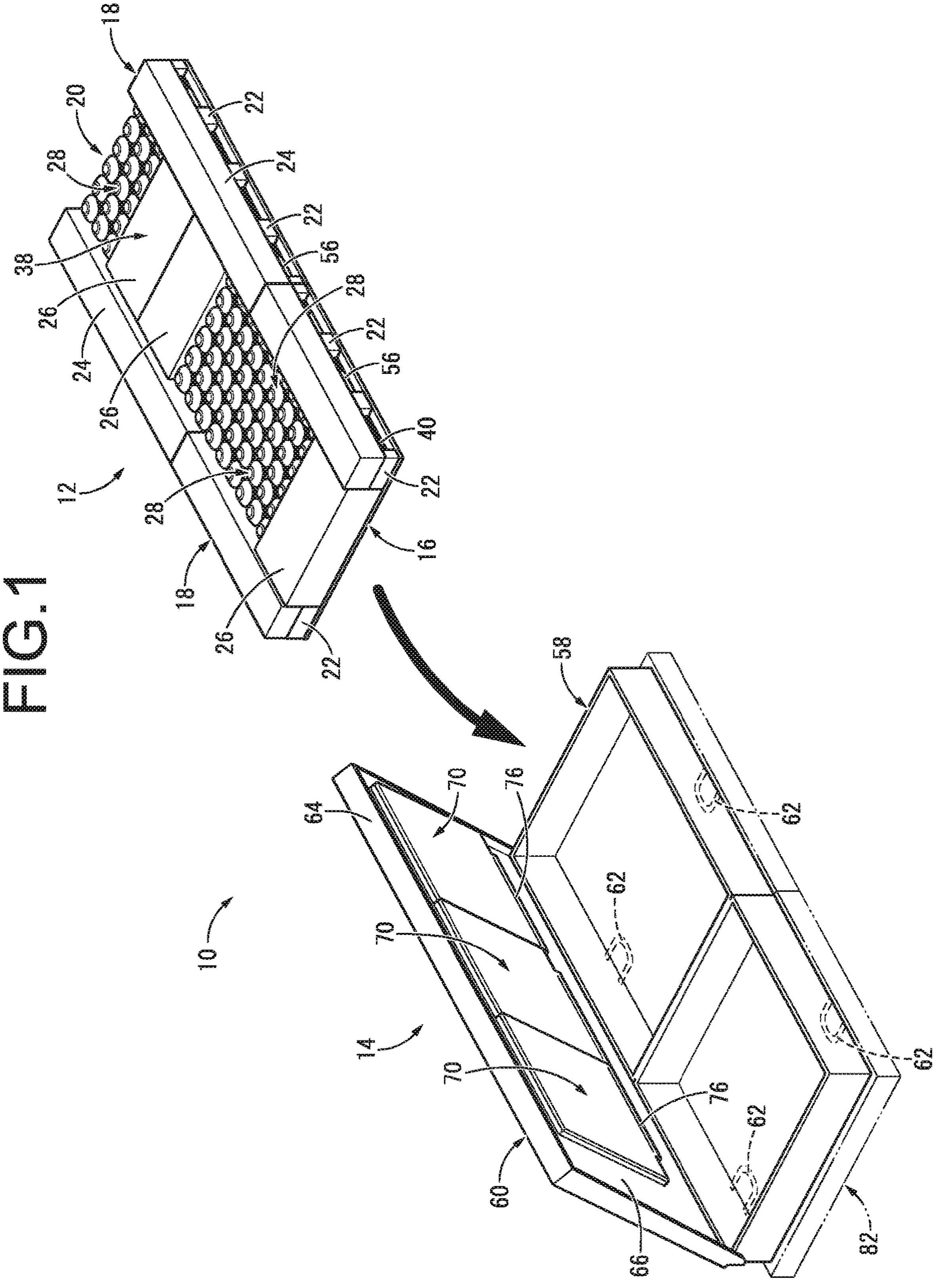
FIG. 1 is a perspective view showing a mattress as a first embodiment of the present invention in a state before a mattress main body is housed within a mattress cover.

There will be hereafter described embodiments of the present invention while referring to the drawings.

FIG. 1 shows a mattress 10 as a first embodiment of the present invention. The mattress 10 has a structure wherein a mattress main body 12 is covered by a mattress cover 14. FIG. 1 shows the mattress main body 12 and the mattress cover 14 as separated for easiness in view. In the following descriptions, the up-down direction means the up-down direction in FIG. 2, which is the vertical direction.

Figure 2:
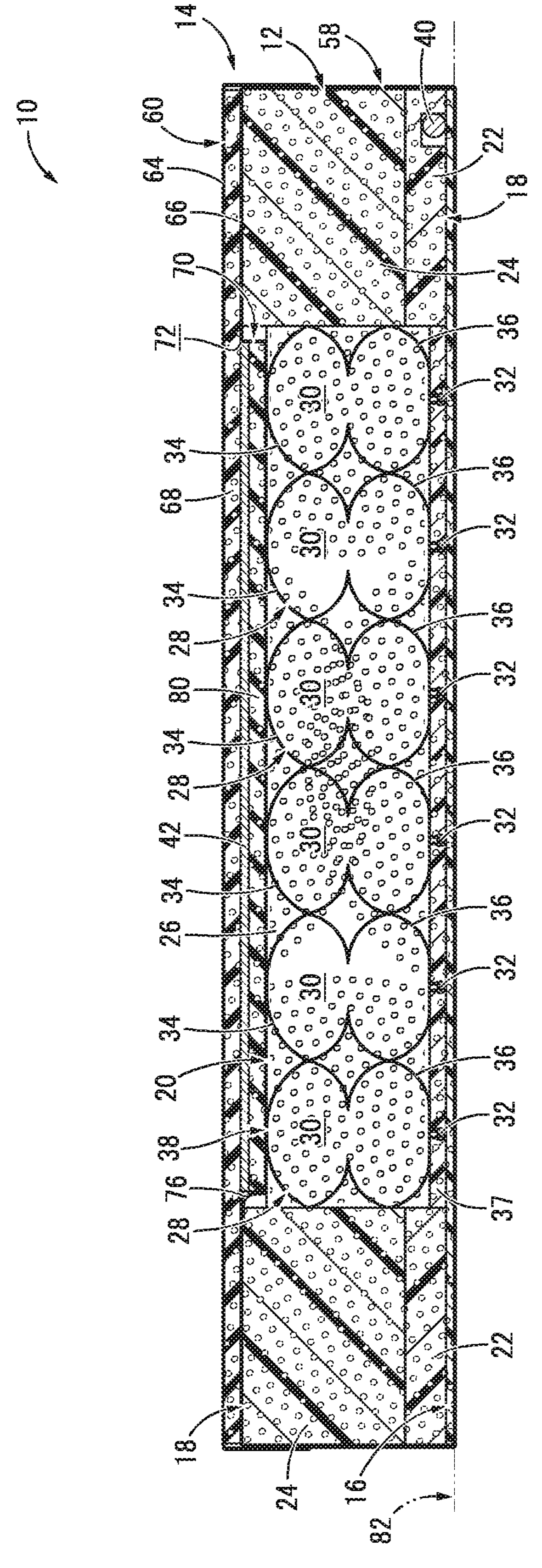
FIG. 2 is a longitudinal cross sectional view of the mattress shown in FIG. 1.

More specifically, the mattress main body 12 has, as FIGS. 1 and 2 show, a base plate 16 whose shape is approximately a rectangular plane plate, end seat parts 18, 18 disposed on the base plate 16 at both edges in the width direction, i.e., the left-right direction in FIG. 2, and a cushion part 20 disposed on the base plate 16 between those end seat parts 18, 18.

The base plate 16 is formed of a urethane foam including close cells with a low foaming ratio, which has comparative hardness, or the like, for example. The base plate 16 undergoes elastic deformation to a certain extent under a load exerted by people like a user and a caregiver, or a nursing attendant, while it is less likely to deform than a superficial cushion 68, a retaining cushion 80, and the like, which will be described later. The base plate 16 is divided at the middle part in the length direction, namely the direction orthogonal to the paper face of FIG. 2, into a head side part and a leg side part.

The end seat part 18 is formed of the same material as that of the base plate 16. The end seat part 18 includes a plurality of pillar lower parts 22, which are disposed on the edges in the width direction of the base plate 16 at prescribed intervals in the length direction, and a beam upper part 24, which is put on the pillar lower parts 22 and extends continuously in the length direction. The end seat part 18 is divided at a position corresponding to the division position of the base plate 16, into a head side part and a leg side part.

The cushion part 20 is constituted by three elastic support bodies 26, 26, 26 and many cells 28, 28, . . . , 28. The elastic support body 26 is formed of the same material as those of the base plate 16 and the end seat part 18, with a rectangular block shape extending in the width direction. In the present embodiment, two elastic support bodies 26, 26 are disposed adjacently in the length direction at a part for supporting the back of the user, which is not shown. On the other hand, one elastic support body 26 is disposed at a part for supporting the legs of the user, which are not shown.

The cell 28 has a shape of a hollow bag formed of a synthetic resin film etc. and has a fluid chamber 30 inside, as FIG. 2 shows. This fluid chamber 30 is filled with a fluid, and fluid supply and exhaust is possible with respect to the fluid chamber 30 through a port 32 provided at a lower end of the cell 28. The cell 28 is capable of extension/contraction in the up-down direction due to the supply and exhaust of the fluid with respect to the fluid chamber 30. The fluid inside the fluid chamber 30 is under no special limitation and various gases and liquids can be adopted, although air is used as the fluid in this embodiment.

The cell 28 of this embodiment has a structure wherein an upper bag body 34 and a lower bag body 36 are disposed one on the other as overlapped, and they have through holes formed at the center portions which are overlapped with each other, thereby forming the fluid chamber 30. Consequently, the cell 28 has a shape including two bulges with a constriction at the vertically medial portion. This structure improves deformation followability of a support surface 38, which will be described later, in relation to the user's body superficial shape, while increasing extension/contraction stroke in the up-down direction of the cell 28.

This cell 28 is, as shown in FIG. 1, disposed between the end seat parts 18, 18 in the width direction, and positioned out of the three elastic support bodies 26, 26, 26 in the length direction, and a plurality of cells 28 are arranged two dimensionally. In the present embodiment, six rows of the cells 28 are arranged in the width direction, and eighteen cells 28 are disposed in the part that supports the user's head, while fifty four cells 28 are disposed in the part that supports the user's waist and legs. The plurality of cells 28 can be each disposed separately, as well. However, in the present embodiment, the ports 32 of the cells 28 protruding downward are fixed to a connection sheet 37 formed of a urethane foam etc., whereby the cells 28 are positioned with respect to one another and can be handled in whole together.

Thus, the three elastic support bodies 26, 26, 26 and the plurality of cells 28 are disposed on the base plate 16 between the end seat parts 18, 18 in the width direction, thereby constituting the mattress main body 12. The upper face of this mattress main body 12 is the support surface 38, that is, the support surface 38 is constituted by including the upper faces of the cells 28. The end seat parts 18, 18 of this embodiment are areas on which the user sits and the caregiver, or the nursing attendant puts their hand and knee when the user moving from on the mattress 10 into a wheelchair, for example, and they has comparative hardness and a stable shape. Consequently, by lying on the center part in the width direction of the support surface 38 that is constituted by the cushion part 20, the user obtains excellent cushioning, or the body pressure dispersibility in other words.

To the respective port 32 of each cell 28, a not-shown distal hose is connected. The distal hose extends outside in the width direction to be connected with the conduit of an extension line 40, which extends in the length direction through the pillar lower parts 22 of the end seat part 18. This conduit of the extension line 40, which is omitted in the drawings, extends outside from the leg side edge of the end seat part 18 and connects with a pump and an air outlet, which are not shown either. This makes it possible to selectively perform air supply into the fluid chamber 30 using the pump and air exhaust from the fluid chamber 30 into the atmosphere. By controlling air supply and exhaust in relation to the fluid chamber 30, it is possible to control the extension and contraction of the cell 28 accordingly. The extension line 40 of the present embodiment is constituted by a hollow tubular conduit, an electrical wiring, and the like, although the extension line 40 is shown in the drawings omitting the detailed structure, for easiness in view.

Figure 3B:
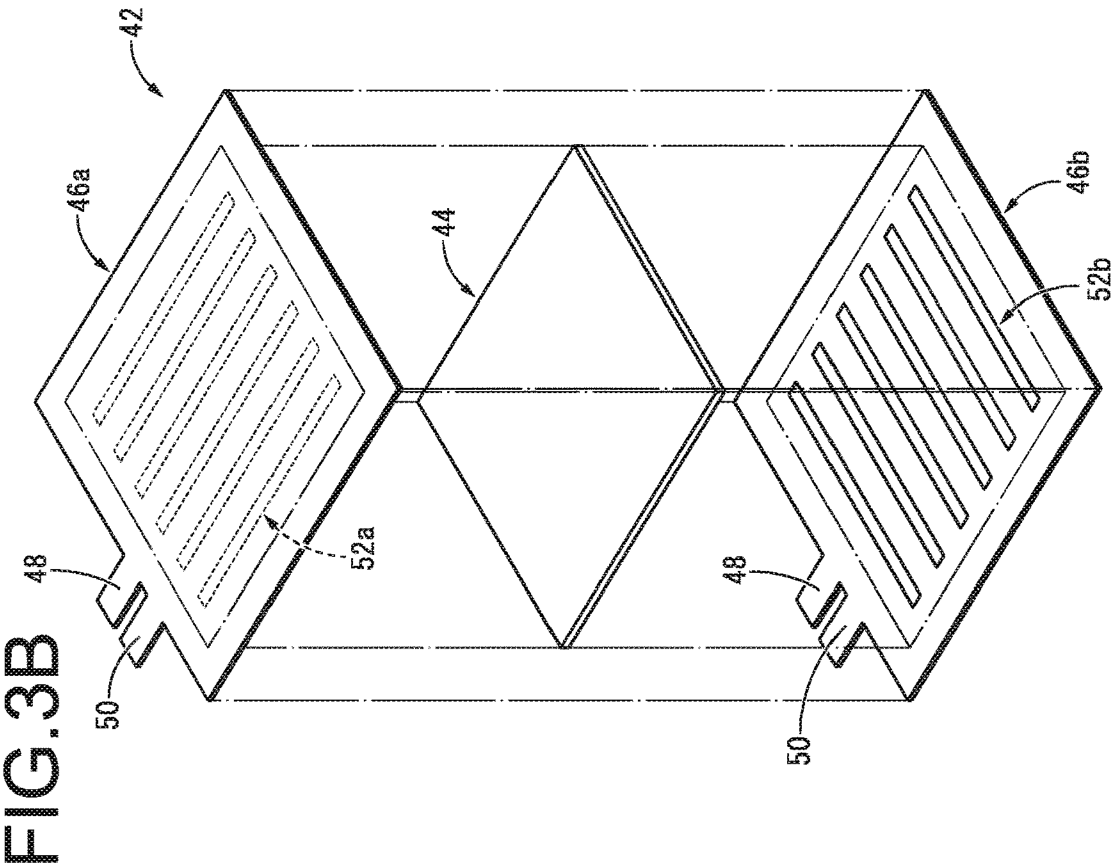
Figure 3A:
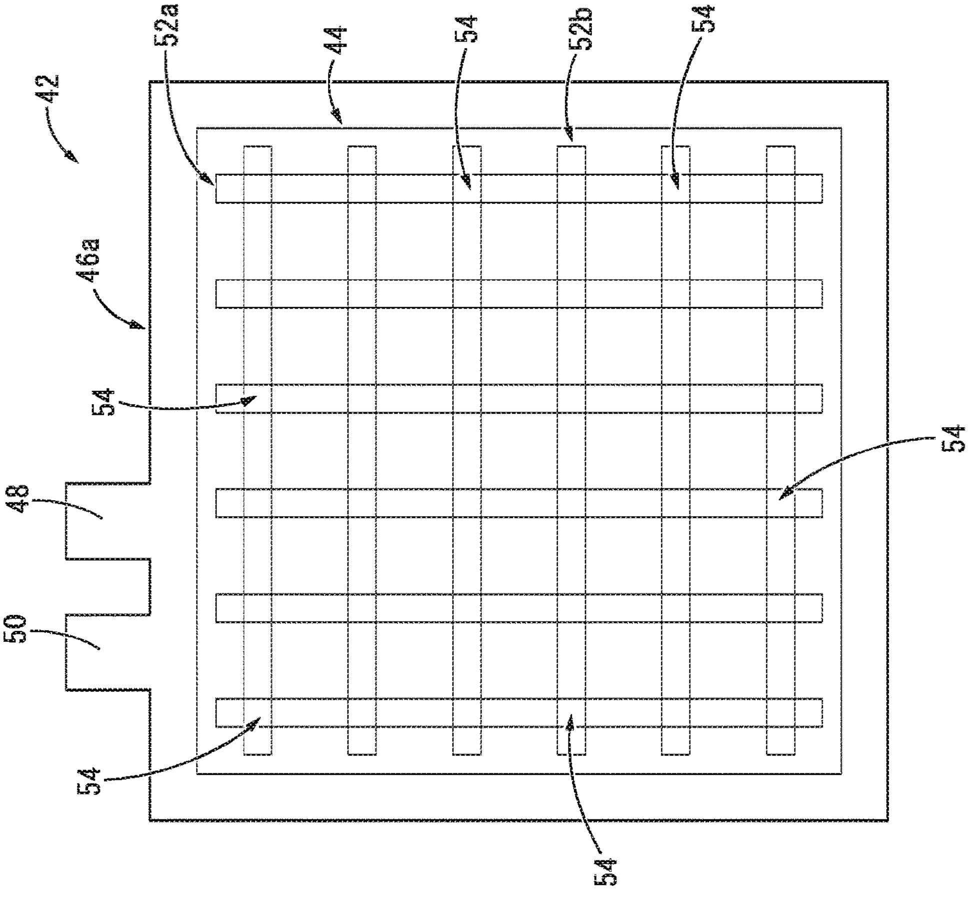

The extension and contraction of the cell 28 is controlled based on detection results of a pressure sensor 42, which detects the pressure exerted on the support surface 38. The pressure sensor 42 whose whole shape is a flexible sheet has a structure wherein to one surface of a dielectric layer 44 formed of an elastic body, an elastomer sheet 46*a* is superposed, while to the other surface thereof, an elastomer sheet 46*b* is superposed, as FIGS. 3A and 3B show.

The dielectric layer 44 is formed of such an electrically insulative elastomer, which is an elastic material, as a rubber or a resin, with a shape of a plate or a sheet. The dielectric layer 44 is capable of extension/contraction elastically in the planar direction, and capable of bending, or flexural deformation elastically in the thickness direction. Preferably used as the forming material of the dielectric layer 44 are silicone rubber, acrylonitrile-butadiene copolymer rubber, acrylic rubber, epichlorohydrin rubber, chlorosulfonated polyethylene, chlorinated polyethylene, urethane rubber, polyethylene resin, polypropylene resin, polyurethane resin, polystyrene resin, polyvinyl chloride-polyvinylidene chloride copolymer, ethylene acetate copolymer, and the like, for example. Moreover, the dielectric layer 44 may be a foam body, and with required dielectric constant and softness kept, the foam body is not always limited to one of uniformity by close cells, and it may be one of randomicity by open cells, for example. The thickness, the forming material and the like of the dielectric layer 44 are set as appropriate depending on relative dielectric constant and softness required in a pressure detection part 54, which will be described later.

The elastomer sheet 46*a* and the elastomer sheet 46*b* are formed of substantially the same material and with substantially the same shape as those of one another. The elastomer sheets 46*a* and 46*b* are electrically insulative sheets formed of an elastomer like a rubber elastic body or a resin, having a substantially rectangular shape in a plan view for this embodiment. On the elastomer sheets 46*a*, 46*b*, a pair of connecting pieces 48, 50 are arranged adjacently in a side on the periphery to protrude peripherally outward. The forming material of the elastomer sheets 46*a*, 46*b* is not especially limited. However, preferably used are silicone rubber, ethylene-propylene copolymer rubber, natural rubber, styrene-butadiene copolymer rubber, acrylonitrile-butadiene copolymer rubber, acrylic rubber, epichlorohydrin rubber, chlorosulfonated polyethylene, chlorinated polyethylene, urethane rubber, polyester resin, polyether urethane resin, polycarbonate urethane resin, polyvinyl chloride acetate copolymer, phenol resin, acrylic resin, polyamide-imide resin, polyamide resin, nitrocellulose, modified celluloses, and the like, for example. The elastomer sheets 46*a*, 46*b* are transparent in the drawings for easy understanding, but they may be opaque.

Moreover, on the lower face of the elastomer sheet 46*a*, electrodes 52*a* are formed, while on the upper face of the elastomer sheet 46*b*, electrodes 52*b* are formed. The electrodes 52*a*, 52*b* are both formed from a rubber, an elastomer or the like that is mixed with a conductive metal or a conductive filler, with a shape of a thin band extending linearly. For each of the electrodes 52*a*, 52*b*, a plurality are formed as arranged in parallel. Those electrodes 52*a* and electrodes 52*b* extend as inclined to one another, and they extend in directions substantially perpendicular to each other in this embodiment.

Furthermore, the elastomer sheets 46*a*, 46*b* extend further outside than the disposition area of the electrodes 52*a*, 52*b*. On the outside of the electrodes 52*a*, 52*b* in the respective elastomer sheets 46*a*, 46*b*, a not-shown printed wiring is printed using a conductive material. The printed wiring of the elastomer sheet 46*a* extends from an end of the electrode 52*a* to one of the connecting pieces, i.e. 48, while the printed wiring of the elastomer sheet 46*b* extends from an end of the electrode 52*b* to the other of the connecting pieces, i.e. 50. The printed wirings can be obtained for example as wiring patterns that are printed on the faces of the elastomer sheets 46*a*, 46*b* using a conductive ink. In addition, the electrodes 52*a*, 52*b* may be formed by printing them using a conductive ink formed from a conductive elastomer, on the elastomer sheets 46*a*, 46*b* as well as the printed wirings. Also, the elastomer sheets 46*a*, 46*b* are fixed to one another by an adhesive, an adhesive tape, or the like in the outer peripheral edge out of the disposition areas of the electrodes 52*a*, 52*b* and the forming areas of the printed wirings.

The elastomer sheet 46*a* and the elastomer sheet 46*b* of this structure are overlapped to the dielectric layer 44 from above and below, respectively. This disposes the electrode 52*a* of the elastomer sheet 46*a* and the electrode 52*b* of the elastomer sheet 46*b* as opposed to each other having the dielectric layer 44 in between and as intersecting. At the part where the electrode 52*a* and the electrode 52*b* are opposed to one another through the dielectric layer 44 while intersecting, a capacitor is constituted, thereby constituting the pressure detection part 54. Note that FIG. 3A shows the dielectric layer 44 and the electrodes 52*a*, 52*b* with fine lines.

At the part where these electrodes 52*a*, 52*b* are opposed to one another while intersecting, namely the pressure detection part 54, a pressure, which is applied to the layered direction of the dielectric layer 44 and the elastomer sheet 46*a*, 46*b*, i.e., the up-down direction, deforms the dielectric layer 44. This shortens the distance between the electrodes 52*a*, 52*b*, so that the electrostatic capacity of the pressure detection part 54 under the input changes. Therefore, by detecting the change of the electrostatic capacity in each pressure detection part 54, it is possible to detect the pressure exerted on each pressure detection part 54. Using a plurality of pressure detection parts 54 enables detection of distribution of the pressure input upon the support surface 38. In short, the pressure sensor 42, wherein each intersection part of the electrodes 52*a*, 52*b*, or each pressure detection part 54, functions as a capacitance type pressure detection element, is a capacitance type sensor that detects pressure distribution on the basis of detection results of all the pressure detection elements.

A control device 56 is disposed between the pillar lower parts 22 of the end seat part 18 in the length direction, and the electrodes 52*a*, 52*b* are electrically connected to the control device 56 via the printed wirings such that the electrodes 52*a*, 52*b* are supplied with electricity for detection from the control device 56. Moreover, the control device 56 is connected to the electric wirings of the extension line 40, through which to an external power supply, a computing unit and the like, which are not shown.

The pressure sensor 42 of this structure is disposed on the support surface 38 of the mattress main body 12 by the mattress cover 14. The mattress cover 14 whose whole shape is a hollow, substantially-rectangular bag, which comprises a lower cover 58 and an upper cover 60 as a support surface cover, can house the mattress main body 12 between the lower cover 58 and the upper cover 60, as FIGS. 1 and 2 show.

The lower cover 58 is formed of a synthetic resin sheet or a fabric etc. in a bag shape opening upward, and can cover the bottom surface and the outer peripheral surface of the mattress main body 12, which is substantially a rectangular parallelepiped in its entirety. As FIG. 1 shows with dotted lines, the lower face of the lower cover 58 is provided with handles 62 at the both ends in the width direction. By pulling the handles 62 out sideward and gripping them, the mattress 10 can be carried easily.

The lower cover 58 is divided in the length direction at the position corresponding to the division position for the base plate 16 and the end seat parts 18, 18 of the mattress main body 12. In the lower cover 58 of the present embodiment, each of the head side housing part for housing the head side part of the mattress main body 12 and the leg side housing part for housing the leg side part of the mattress main body 12 has a bag shape opening upward. Additionally, the lower cover 58 of this embodiment has those head side housing part and leg side housing part integrally formed to be mutually continuous at the openings so that those head side housing part and leg side housing part can tilt in a hinge way around the connection part. The lower cover 58 is shown in a rectangular box shape in the drawings for easiness in view, although the lower cover 58 is formed of a soft material to readily undergo deformation. For example, the peripheral wall of the lower cover 58 may be one that cannot stand alone under the action of the gravity.

Figure 4:
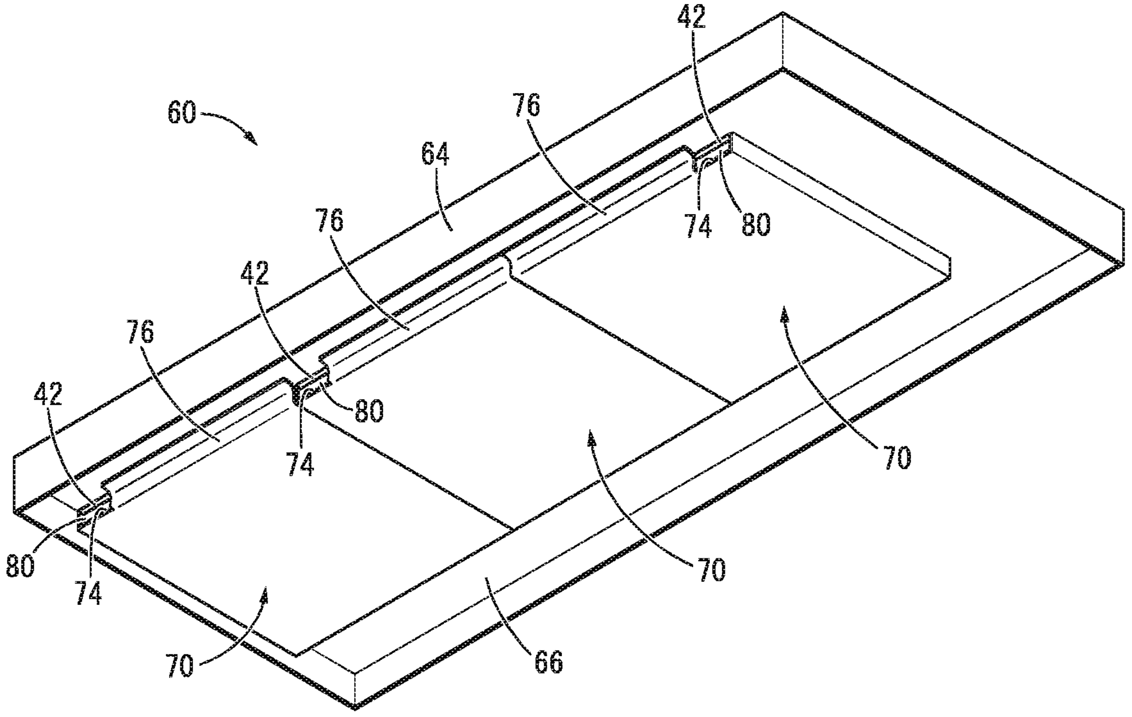
FIG. 4 is a perspective view of an upper cover constituting the mattress shown in FIG. 1.

The upper cover 60 is formed of a synthetic resin sheet, a fabric or the like as well as the lower cover 58. As shown in FIGS. 1 and 4, the upper cover 60 has a shallow, substantially-rectangular bag shape opening downward, and it can cover and close the opening of the lower cover 58. By so doing, the upper face of the mattress main body 12 housed in the lower cover 58 is covered by the upper cover 60, whereby the mattress main body 12 is stored in the internal space of the mattress cover 14. The mattress cover 14 including the upper cover 60 is positioned with respect to the mattress main body 12, and the upper cover 60 covers the support surface 38 of the mattress main body 12. In the present embodiment, a portion of the peripheral wall of the upper cover 60 is fixed on the upper end of the peripheral wall of the lower cover 58. The upper cover 60 displaces with respect to the lower cover 58 in a hinge way around the fixing part, thereby enabling opening and closing of the opening of the lower cover 58.

Figure 5:
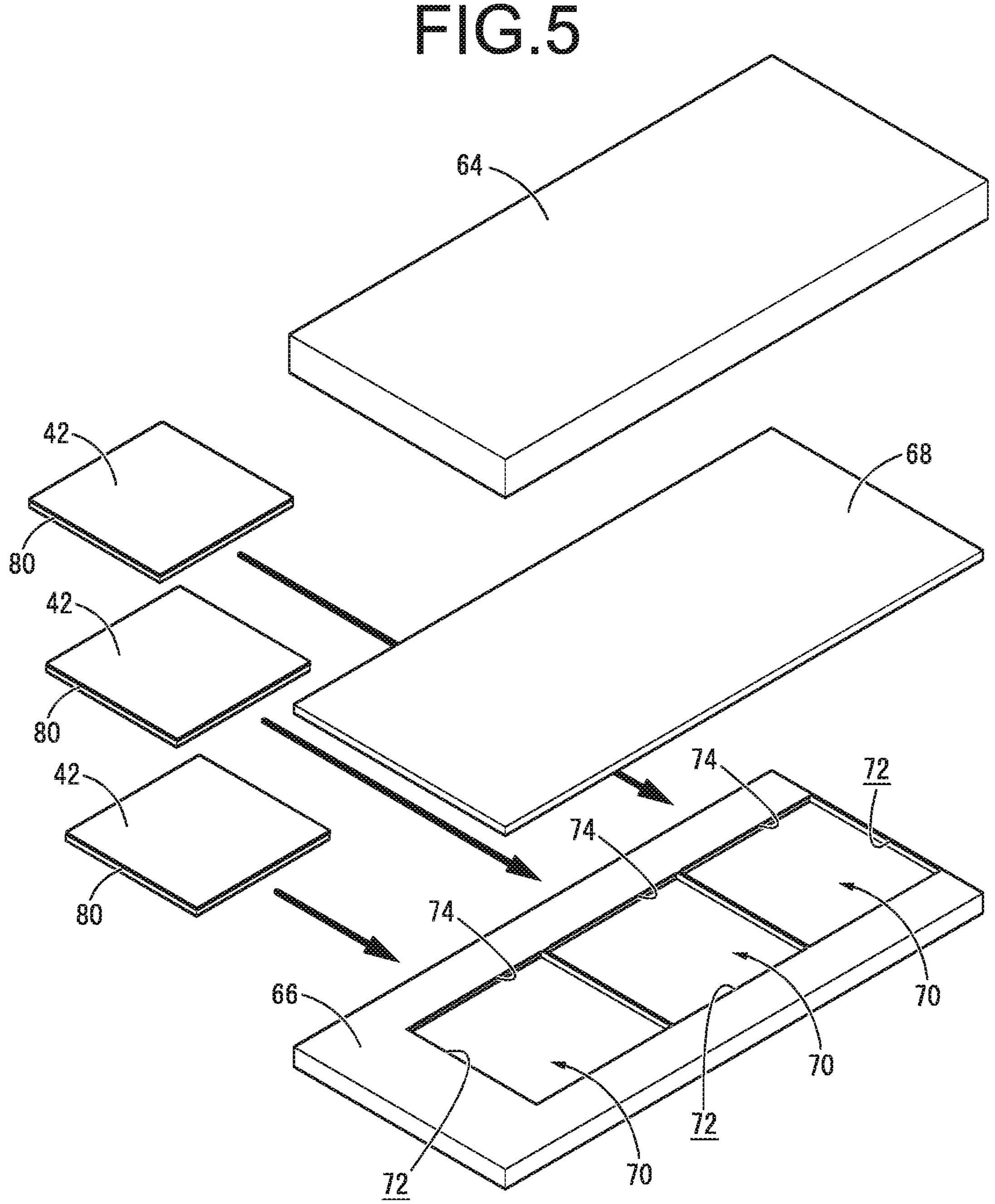
FIG. 5 is an exploded perspective view of the upper cover shown in FIG. 4.

Besides, the upper cover 60 has a double structure having an outer layer 64 and an inner layer 66 as shown in FIGS. 2 and 5. Between the outer layer 64 and the inner layer 66 in the up-down direction, the plate-shaped superficial cushion 68 formed of a flexible soft urethane foam etc. is stored.

As FIGS. 1 and 4 show, for the lower face of the upper cover 60, three pocket bodies 70 are provided as positioning members. The pocket body 70, which has a flat, hollow bag shape corresponding to the pressure sensor 42, includes a sensor housing cavity 72 inside. The pocket body 70 of this embodiment is integrally provided to the upper cover 60 in an undetachable way, and formed by having the inner layer 66 be partially concave like protruding downward and covering the upper opening of the concave part with the superficial cushion 68 and the outer layer 64. Note that the pocket body 70 is formed of such a material as a synthetic resin sheet or a fabric with flexibility that is elastically deformable in the planar direction in the same way as the inner layer 66 of the upper cover 60.

Moreover, the pocket body 70 has a sensor inlet 74 as an opening part that opens to a side face in the width direction. The sensor inlet 74 is formed with a shape and a size corresponding to the pressure sensor 42. Through the sensor inlet 74, the pressure sensor 42 can be inserted into the sensor housing cavity 72 of the pocket body 70, while the pressure sensor 42 can be got out of the sensor housing cavity 72 to be removed from the pocket body 70. In sum, the sensor housing cavity 72 of the pocket body 70 opens to the outside via the sensor inlet 74, which opens on the side.

Furthermore, the pocket body 70 has a lid body 76 integrally formed therewith as an opening and closing member. This lid body 76 is integrally formed with the inner layer 66 at the opening peripheral part of the sensor inlet 74 extending out sideward, and it can close at least one portion of the sensor inlet 74 by covering. Additionally provided is a not-shown retainer that retains the projecting end part of the lid body 76 and the lower face of the inner layer 66 in the vicinity of the sensor inlet 74 in relation to each other. With the retainer, the state where the lid body 76 covers the opening of the sensor inlet 74 can be maintained, while the covering of the sensor inlet 74 by the lid body 76 may be canceled. Note that as the retainer, it is possible to use a hook-and-loop fastener, a button, a snap, a band, and the like, for example. This retainer is provided on a position out of the support surface 38 in the width direction when the lid body 76 closes the opening of the sensor inlet 74 as FIG. 2 show. This realizes good sleeping comfort without giving hard touch to the user lying on the support surface 38.

Within the pocket body 70, the pressure sensor 42 is housed. Specifically, the pressure sensor 42 is inserted through the sensor inlet 74 between the inner layer 66 and the superficial cushion 68 in addition to the outer layer 64, and thus housed within the pocket body 70. The sensor inlet 74 of the pocket body 70 storing the pressure sensor 42 is closed using the lid body 76 and the retainer, so that the pressure sensor 42 is kept in a stored state without unintentionally getting out of the pocket body 70.

Thus, the pressure sensor 42 is housed in the sensor housing cavity 72 of the pocket body 70 in a non-adhesive manner to be movable in the planar direction within the sensor housing cavity 72 of the pocket body 70, under limitation of the movement amount in the planar direction by the pocket body 70. In brief, the pressure sensor 42 is positioned as movable by a prescribed amount in the planar direction in relation to the upper cover 60 owing to the pocket body 70. Also, the pocket body 70 is provided at the center in the width direction of the upper cover 60. Consequently, when the upper cover 60 covers the upper face of the mattress main body 12, the pressure sensor 42 housed within the pocket body 70 is positioned on the support surface 38.

It is desirable that storing of the pressure sensor 42 in the sensor housing cavity 72 of the pocket body 70 limits the amount of the movement of the pressure sensor 42 in the planar direction within 15 mm when no load is input upon the pocket body 70. More preferably, the amount of the movement of the pressure sensor 42 in the planar direction is limited within 10 mm. This makes the gap between the pressure detection results of the pressure sensor 42 and the position where the pressure acts in fact on the support surface 38 of the mattress main body 12 small enough.

It is also desirable that storing the pressure sensor 42 in the sensor housing cavity 72 of the pocket body 70 allows the movement of the pressure sensor 42 in the planar direction by 1 mm or longer when no load is input upon the pocket body 70. More preferably, the pressure sensor 42 is allowed to move in the planar direction by 3 mm or longer. This allows the flexural deformation of the pressure sensor 42 enough, thereby avoiding the pressure sensor 42 from damaging the softness of the upper cover 60.

Besides, with the present embodiment, the retaining cushion 80 is housed within the pocket body 70 together with the pressure sensor 42. The retaining cushion 80 is formed of a soft urethane foam in a thin plate shape or the like in the same way as the superficial cushion 68, and can readily undergo elastic compression deformation and bending deformation, or flexure in the thickness direction. As FIG. 2 shows, the retaining cushion 80 is superposed to the pressure sensor 42 in the thickness direction and arranged on the side of the pressure sensor 42 close to the support surface 38, namely the lower side. This disposes the pressure sensor 42 between the superficial cushion 68 and the retaining cushion 80, which elastically position the pressure sensor 42 in the sensor housing cavity 72 of the pocket body 70 while allowing the pressure sensor 42 to undergo bending, or flexural deformation elastically by their elastic deformation. The movement in the planar direction in the sensor housing cavity 72 for the pressure sensor 42 and the retaining cushion 80 may be allowed by making the thickness sum of the pressure sensor 42 and the retaining cushion 80 smaller than the up-down dimension of the sensor housing cavity 72 of the pocket body 70, for example.

In the upper cover 60, the three pocket bodies 70, 70, 70 are arranged in the length direction, and the respective sensor housing cavities 72 for the three pocket bodies 70, 70, 70 are mutually separate. Additionally, each of the three pocket bodies 70, 70, 70 houses the pressure sensor 42 and the retaining cushion 80, thereby shortening the length of the pressure sensor 42 and the retaining cushion 80 housed in each pocket body 70. That is, it is possible to make the length for the pressure sensor 42 and the retaining cushion 80 roughly one third of the whole length for the target area of the pressure detection. However, it is also possible to dispose one pressure sensor for the whole area for which pressure detection is necessary in the support surface 38. For this situation, the upper cover 60 is provided with only a single pocket body having an internal space like being formed by connecting the sensor housing cavities 72, 72, 72 of the three pocket bodies 70, 70, 70 of this embodiment in the length direction.

The sensor housing cavity 72 of the pocket body 70 is a space of roughly the same size as the size of the pressure sensor 42 and the retaining cushion 80, but desirably slightly larger than the size of the pressure sensor 42 and the retaining cushion 80. This size setting can avoid the pressure sensor 42 from being strongly clasped and cramped in the thickness direction. In addition, it allows extension deformation in the planar direction accompanying up-down compression deformation of the retaining cushion 80, thereby sufficiently allowing flexural deformation of the pressure sensor 42.

The mattress 10 of this structure is laid on a bed 82 and thus disposed between the user and the bed 82 so as to disperse the body pressure of the user. Especially in the mattress 10 of the present embodiment, the support surface 38 is partially constituted by the cells 28 and the cells 28 undergo extension and contraction depending on air supply and exhaust with respect to the fluid chamber 30, thereby enabling active deformation of the support surface 38. The extension and contraction of the cell 28 is controlled based on the detection results of the pressure sensor 42. This avoids large pressure from acting locally upon the user, thereby realizing good sleeping comfort owing to the dispersion of the body pressure.

Here in the mattress 10 of this embodiment, the pressure sensor 42 disposed on the support surface 38 of the mattress main body 12 is positioned at a prescribed position on the support surface 38 by the pocket body 70 of the mattress cover 14, thereby improving the detection accuracy of the pressure by the pressure sensor 42. Specifically, the pressure sensor 42 is stored in the pocket body 70, so that it is positioned with respect to the upper cover 60. On the other hand, the mattress main body 12 is stored in the mattress cover 14 including the upper cover 60, so that the upper cover 60 is positioned with respect to the mattress main body 12. As a result, the pressure sensor 42 is positioned in relation to the mattress main body 12, whereby the pressure sensor 42 is positioned in a prescribed position on the support surface 38 of the mattress main body 12.

Especially since the support surface 38 partially comprises the plurality of cells 28 and the pressure sensor 42 has a structure wherein the plurality of pressure detection parts 54 are arranged two dimensionally, effective pressure detection using the part of the support surface 38 that is constituted by the cells 28 requires relative positioning of the upper faces of the cells 28 and the pressure detection parts 54 of the pressure sensors 42. Therefore, positioning the pressure sensor 42 with respect to the support surface 38 using the pocket body 70 enables precise pressure detection in combination of the fluid-cell mattress main body 12 whose support surface 38 is constituted by the plurality of cells 28 and the pressure sensor 42 that can detect pressure by the plurality of pressure detection parts 54. Besides, each pressure detection part 54 of the pressure sensor 42 is positioned with respect to the upper face of the respective cell 28 relatively in the planar direction. Consequently, it is not necessary to provide a considerably large number of pressure detection parts 54 densely for the pressure sensor 42, and it is possible to adopt the inexpensive pressure sensor 42 that can be manufactured easily, as well as a simple computing unit for detection signals etc.

Moreover, the pressure sensor 42 is housed within the pocket body 70 in a non-adhesive manner, whereby the pressure sensor 42 can move in the planar direction in the sensor housing cavity 72 of the pocket body 70. The pressure sensor 42 is permitted to move relative to the upper cover 60, while the allowable amount of the movement is limited by the pocket body 70. Thus, the pressure sensor 42 is permitted to move relative to the support surface 38 of the mattress main body 12 within a range confined to the sensor housing cavity 72 of the pocket body 70, and it is positioned with respect to the support surface 38 without being restrained.

Figure 6:
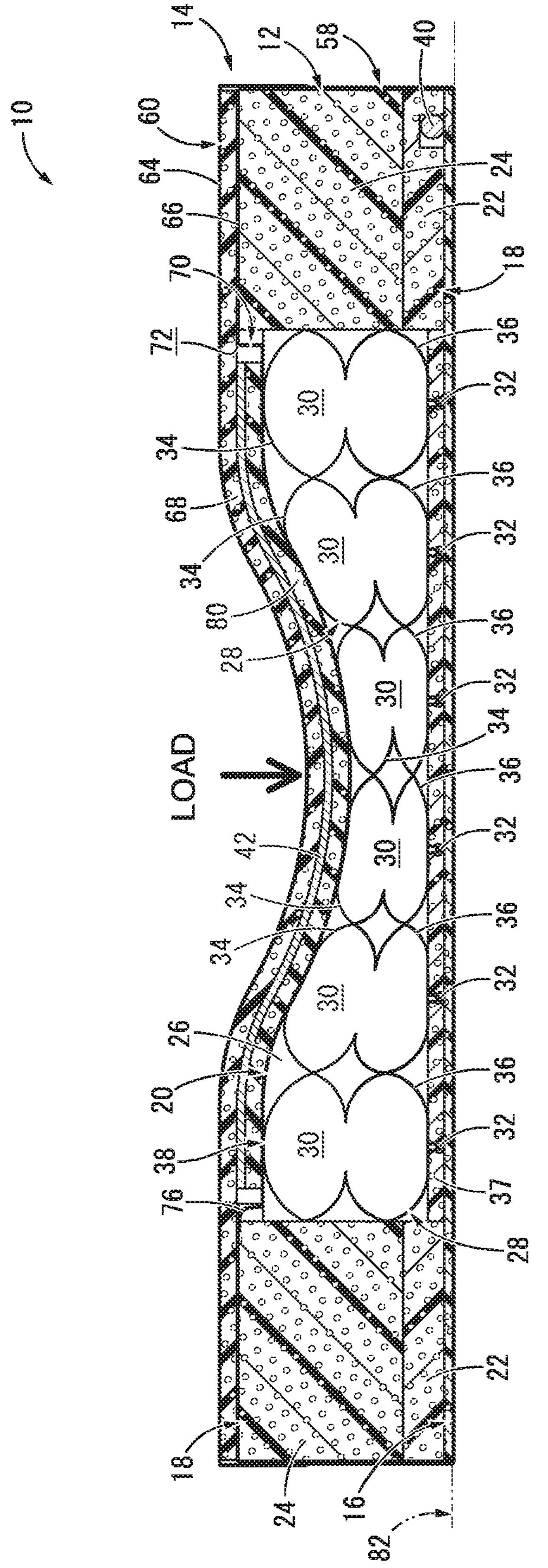
FIG. 6 is a longitudinal cross sectional view of the mattress shown in FIG. 1, showing a state upon a load input on a support surface.

The pressure sensor 42 is thus positioned with respect to the support surface 38 with room for a certain extent of relative movement, so that the pressure sensor 42 hardly hinders the deformation of the upper cover 60. As FIG. 6 shows, a load input downward upon the support surface 38 causes contraction deformation of the cell 28, so that the support surface 38 is deformed in a concave shape, and accordingly to it, the upper cover 60 is deformed to be concave downward. The pressure sensor 42 is stored in the sensor housing cavity 72 in a non-adhesive manner relative to the pocket body 70 of the upper cover 60, and hardly extends in comparison with the superficial cushion 68, the retaining cushion 80, the inner layer 66, and the outer layer 64, which are the components of the upper cover 60. As a result, during flexural deformation of the upper cover 60 and the pressure sensor 42 by a load input, the pressure sensor 42 is less likely to extend than the pocket body 70, whereby the edges of the pressure sensor 42 undergo flexural deformation while moving inward in the width direction in the sensor housing cavity 72. By so doing, the pressure sensor 42 whose extension/contraction ratio is smaller than those of the components of the upper cover 60 could undergo sufficient flexural deformation following after the upper cover 60 deforming in a flexural manner with extension as well. This could avoid the pressure sensor 42 from hampering the deformation of the upper cover 60 that is in contact with the user. Therefore, the upper cover 60 deforms depending on the superficial shape of the user's body with excellent followability, thereby effectively dispersing the body pressure and giving the user good sleeping comfort.

The amount of the movement of the edges of the pressure sensor 42 with respect to the upper cover 60 in the planar direction caused by the above-described flexural deformation is desirably limited to within 10 mm. More preferably, the amount of the movement in the planar direction is limited to within 7 mm. According to this, it is possible to prevent considerable deviation of the pressure sensor 42 under flexural deformation when used with respect to the support surface 38, accordingly avoiding lower accuracy of the pressure detection. Besides, the movement amount in the planar direction for the center of the pressure detection part 54 in the pressure sensor 42 relative to the diametrical center of the cell 28 is desirably limited to within 12 mm, more preferably within 6 mm. Thus, even if the cell 28 undergoes such deformation as tilting, the positioning gap between the pressure detection part 54 and the cell 28 is kept small enough, thereby providing effective detection accuracy.

Meanwhile, the movement in the planar direction of the edges of the pressure sensor 42 by the flexural deformation is permitted desirably with a size of larger than 1 mm, more preferably with a size of larger than 3 mm. This enables sufficient deformation of the upper cover 60 free from restraint by the pressure sensor 42, as well as good sleeping comfort owing to the body pressure dispersion.

In addition, for the present embodiment, the pressure sensor 42 is clamped in a non-adhesive manner and thus elastically supported between the superficial cushion 68 and the retaining cushion 80. This allows the pressure sensor 42 to move in the planar direction in the sensor housing cavity 72 of the pocket body 70, while elastically positioning it in the thickness direction. Moreover, such strain deformation of the pressure sensor 42 in the sensor housing cavity 72 of the pocket body 70 as wrinkling and folding is avoided, while the flexural deformation of the pressure sensor 42 is allowed owing to the elastic deformation of the superficial cushion 68 and the retaining cushion 80.

The positioning member for positioning the pressure sensor 42 comprises the bag-shaped pocket body 70, so that it is possible to provide the positioning member for the upper cover 60 without having an adverse effect on the softness of the upper cover 60 to be in contact with the user. Additionally, on the side that is nearer the user than the inner layer 66 having the pocket body 70, the superficial cushion 68 is provided, and it is possible to eliminate slight sense of discomfort caused by the pocket body 70.

Besides, since the pocket body 70 is provided for the upper cover 60 that covers the support surface 38, it is possible to easily position the pressure sensor 42 at the prescribed position on the support surface 38, by only covering the support surface 38 with the upper cover 60, without limiting the support surface 38 of the mattress main body 12 to a specific structure. Moreover, the pocket body 70 is integrally formed with the inner layer 66 of the upper cover 60 and provided in an undetachable way to the upper cover 60, whereby the pocket body 70 is stably disposed at a proper position with respect to the upper cover 60. Furthermore, since the pressure sensor 42 is housed in the pocket body 70 to be removable therefrom, when the upper cover 60 and the pocket body 70 get soiled or damaged, it is possible to wash and exchange the upper cover 60 and the pocket body 70 after the pressure sensor 42 is removed from the pocket body 70.

The three pocket bodies 70, 70, 70 are arranged side by side in the length direction, and each of the sensor housing cavities 72 thereof houses the pressure sensor 42. This makes it possible to minimize the size of each pressure sensor 42, thereby reducing the positioning gap of each pressure sensor 42 relative to the support surface 38 and facilitating the manufacture of the pressure sensor 42. In addition, it is also possible to house the pressure sensor 42 selectively in at least one selected out of the three pocket bodies 70, 70, 70, depending on an extent of the user's physique, impediment, illness or injury. Alternatively, it is possible as well to house a plurality of types of pressure sensors 42 with different detection system, e.g., capacitance type, resistance type, electromagnetic induction type, or different detection accuracies within the three pocket bodies 70, 70, 70.

Additionally in the present embodiment, the bed 82 has reclining function by which the upper body of the user is raised, and the mattress 10 disposed on the bed 82 can have the head side part and the leg side part be tilted relative to one another corresponding to reclining of the bed 82. More specifically, for the mattress 10, the mattress main body 12 and the lower cover 58 are respectively divided into the head side part and the leg side part, which can be mutually tilted. Meanwhile, the upper cover 60 has two pocket bodies 70, 70 at the head side part and one pocket body 70 at the leg side part and each of the three pocket bodies 70, 70, 70 stores the pressure sensor 42. Therefore, the two pressure sensors 42, 42 disposed in the head side part can be tilted without being folded following the reclining. This prevents decrease in durability of the pressure sensor 42 caused by the folding in the reclining, decrease in the pressure detection accuracy during the reclining, and the like.

Figure 7:
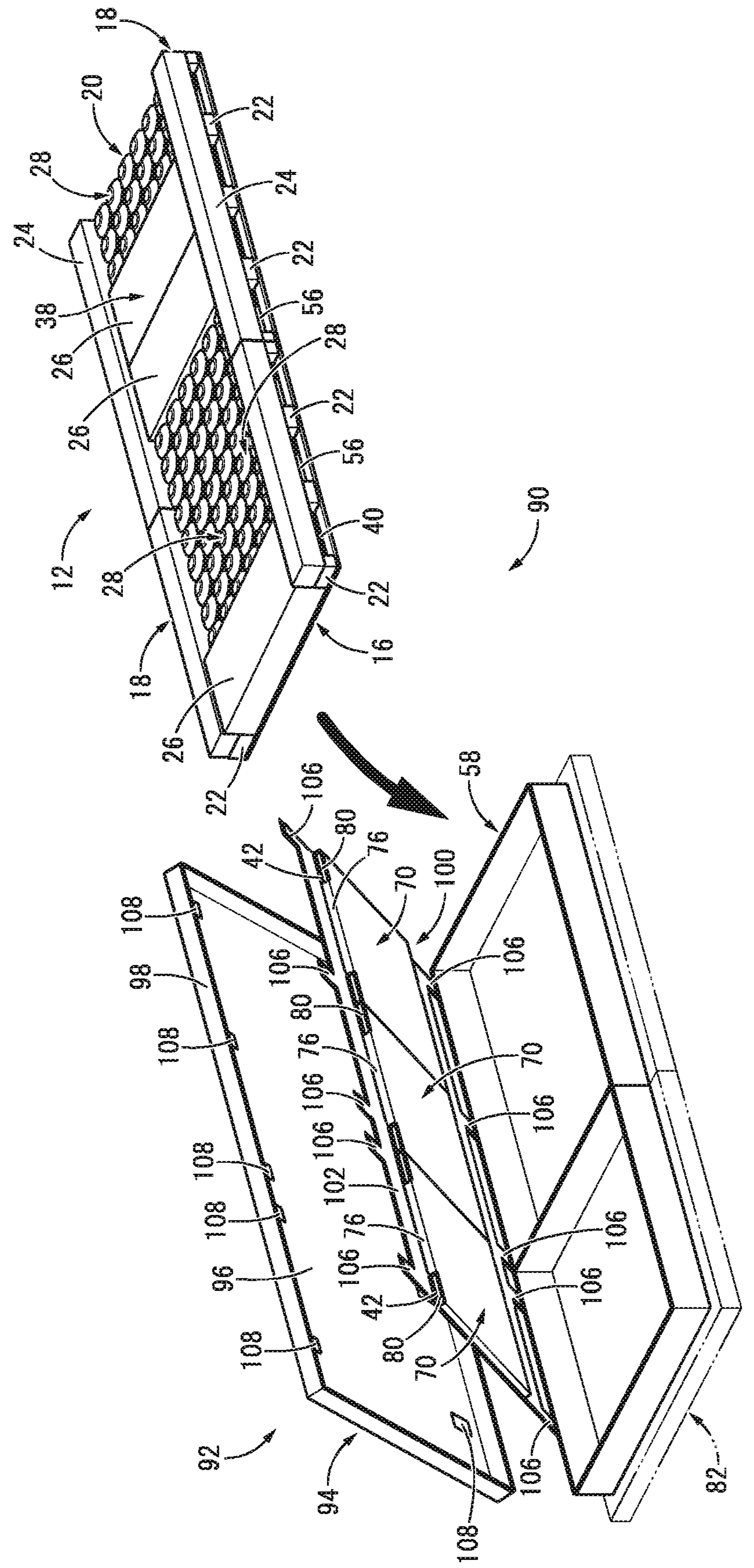
FIG. 7 is an exploded perspective view of a mattress cover constituting a mattress as a second embodiment of the present invention.

FIG. 7 shows a mattress 90 as a second embodiment of this invention. The mattress 90 has a structure wherein the mattress main body 12 is housed within a mattress cover 92. Note that, for members and parts of substantially the same structure as those of the first embodiment, the same code number is given in the drawings, and a description will be omitted.

The mattress cover 92 has a shape of a hollow bag formed of a fabric, a synthetic resin sheet or the like. The mattress cover 92 includes the lower cover 58 that covers the lower face and the outer peripheral face of the mattress main body 12 and an upper cover 94 as a support surface cover that covers the upper face of the mattress main body 12, or the support surface 38.

The upper cover 94 includes an upper base wall 96 that covers the support surface 38 of the mattress main body 12 and a peripheral wall 98 that is connected to the upper part of the peripheral wall of the lower cover 58 as being disposed externally thereabout. Although the drawings do not clearly show, the upper cover 94 of the present embodiment is desired to have a structure with the superficial cushion between the inner layer and the outer layer, in the same way as the upper cover 60 of the first embodiment.

To the upper cover 94, a sensor disposing member 100 is attached. The sensor disposing member 100 includes an attachment sheet 102 that is attached detachably with respect to the upper base wall 96 of the upper cover 94, and the three pocket bodies 70, 70, 70 as positioning members formed integrally with the attachment sheet 102. Note that the pocket body 70 of this embodiment, which has its upper wall constituted by the attachment sheet 102, is formed integrally with the attachment sheet 102.

The attachment sheet 102 has a shape of a substantially rectangular plane corresponding to the shape of the mattress main body 12. Additionally, the attachment sheet 102 has attachment pieces 106 projecting outward in the width direction partially, at a plurality of locations in the length direction. The attachment piece 106 can be attached to the upper base inner face of the upper cover 94 detachably, using an attachment means including a hook-and-loop fastener, a snap, and a band. By so doing, the attachment sheet 102 can be attached to the upper cover 94 detachably. In the present embodiment, hook-and-loop fasteners 108 are provided for the attachment pieces 106 and prescribed positions in the upper base inner face of the upper cover 94. The attachment pieces 106 are each provided in the vicinity of the edges in the length direction of the three pocket bodies 70, 70, 70. Especially for the part where the attachment sheet 102 is folded by the reclining, at locations on both sides of the folded part which are close thereto in the length direction, the attachment pieces 106 are provided to prevent dislodgement of the attachment sheet 102 from the upper cover 94 due to the folding.

This pocket body 70, in the same way as the first embodiment, stores the pressure sensor 42 and the retaining cushion 80 as overlapped with one another. With the pressure sensor 42 and the retaining cushion 80 housed, the opening part of the pocket body 70, namely the sensor inlet 74 is closed by the lid body 76. As a result, these pressure sensor 42 and retaining cushion 80 are kept to be housed in the pocket body 70. This permits the pressure sensor 42 to move in the planar direction in the sensor housing cavity 72 of the pocket body 70, although the amount of the movement in the planar direction is limited by contact with the peripheral wall inner face of the pocket body 70.

With the sensor disposing member 100 including the pocket bodies 70 for housing the pressure sensors 42 and the retaining cushions 80 in the respective sensor housing cavities 72, the attachment piece 106 of the attachment sheet 102 is attached to the upper base inner face of the upper cover 94 with the hook-and-loop fastener 108 detachably in the present embodiment. Consequently, the sensor disposing member 100 is retained to be superposed to the upper base inner face of the upper cover 94, and the pressure sensor 42 housed in each of the pocket bodies 70 is allowed to move in the planar direction relative to the upper cover 94 under limitation for the movement amount in the planar direction.

The upper cover 94 is disposed to cover the opening of the lower cover 58, and the peripheral wall 98 of the upper cover 94 is mutually connected to the peripheral wall of the lower cover 58 by a zipper, a hook-and-loop fastener, a snap, a band, a hook or the like, whereby the hollow-bag-shaped mattress cover 92 is constituted. The mattress main body 12 is stored in the internal space of this mattress cover 92, and the whole surface of the mattress main body 12 is covered by the mattress cover 92.

The mattress cover 92 is attached to the mattress main body 12 in this way, so that the pressure sensors 42, 42, 42 are disposed and positioned on the support surface 38 of the mattress main body 12.

In the mattress 90 with this structure according to the present embodiment as well, the pressure sensor 42 is positioned at the prescribed position on the support surface 38 and it is possible to detect the pressure acting on the support surface 38 with good accuracy. In addition, restraint on the upper cover 94 by the pressure sensor 42 is decreased, thereby realizing flexible deformation of the upper cover 94.

Since the sensor disposing member 100 having the pocket body 70 is attached to the upper cover 94 in an embodiment which makes the sensor disposing member 100 easily removable, when the pocket body 70 gets damaged or the like, it is possible to convert only the sensor disposing member 100 without changing the upper cover 94. Also, it is possible to use materials that are mutually different for the upper cover 94 and the sensor disposing member 100, thereby making it possible to meet the respective required performances for the upper cover 94 and the sensor disposing member 100 to a high degree.

Moreover, in the present embodiment, by providing the hook-and-loop fasteners 108 on the side of the upper cover 94 only at parts corresponding to the attachment pieces 106 in the length direction, the sensor disposing member 100 is easily positioned with respect to the upper cover 94 in the length direction. Note that providing the hook-and-loop fasteners 108 on the side of the upper cover 94 continuously in the length direction, for example, enables the attachment location of the sensor disposing member 100 relative to the upper cover 94 to be adjusted in the length direction. According to this, it is possible to dispose the pressure sensor 42 at an appropriate position in the length direction corresponding to the user's physique or the like.

Although the embodiments of the present invention have been described above, the present invention is not limited by the specific descriptions. For example, in the aforementioned embodiment, the bag-shaped pocket body 70 that houses the pressure sensor 42 is shown as an example of the positioning member that positions the pressure sensor 42. However, the positioning member is not always limited to the bag-shaped one, and it is possible to use a positioning member in a slit shape or a band shape to which the four corners of the pressure sensor 42 are inserted for positioning. Moreover, as a positioning member, it is possible to adopt a structure including the pressure sensor 42 having a hole or a concavity formed at its outer periphery and the upper cover 60 having a protrusion, where the protrusion of the upper cover 60 is inserted in the hole or the concavity of the pressure sensor 42 with a gap. According to this, the pressure sensor 42 is positioned such that it is allowed to move in the planar direction by the gap between the protrusion and the hole or the concavity, while the movement amount in the planar direction of the pressure sensor 42 is limited by the engagement between the protrusion and the hole or the concavity. For this case, the retaining cushion 80 can be omitted.

Also, shown as examples in the above-mentioned embodiments are the mattress covers 14, 92 each of which houses the mattress main body 12 and covers the entire mattress main body 12. For example, it is also possible to use a mattress cover comprising only the support surface cover that covers the upper surface of the mattress main body 12, with the lower cover 58 omitted. For this case, a structure for positioning the support surface cover with respect to the mattress main body 12, e.g. a rubber band, a hook-and-loop fastener, a hook, or a snap can be provided as appropriate.

Moreover, a positioning member separate from the support surface cover as shown in the second embodiment can be attached to the support surface cover in an undetachable way by means of sewing, adhesion, welding or the like.

The arrangement, the number, and the specific shape of the cell 28 shown in the above-described embodiments are under no special limitation, and they can be changed as appropriate depending on the required characteristics of the mattress main body 12 different for each user. Specifically, for example, although the aforesaid embodiments show the cell 28 whose shape has two bulges as an example, it is also possible to use a cell having only one bulge or a cell whose shape has a plurality of bulges which are three or more. It is also possible to use an elongated cell extending by a prescribed length in the width direction or in the length direction. Besides, in the above-mentioned embodiments, the support surface 38 is partially constituted by the cells 28, although the entire support surface 38 can be constituted by the cells 28, for example.

Also, the aforesaid embodiments show an active-control type fluid-cell mattress that assertively controls the extension and contraction for the cell 28 by air supply and exhaust with respect to the fluid chamber 30 of the cell 28 on the basis of the detection results of the pressure sensor 42, as an example. However, this invention can be used for a passive type fluid-cell mattress wherein the fluid chambers 30 of the plurality of cells 28 are mutually communicated and fluid flow is allowed only therebetween, for example.

Furthermore, this invention is applicable not always only to the fluid-cell mattress. It is also possible to use a mattress main body using metal springs such as coil springs or spring steel linear materials instead of air spring of the cells, or a mattress main body whose entirety is formed of a polymeric elastomer like a urethane foam.

What is claimed is:

1. A mattress comprising:

a support surface to support a user;

a mattress main body that constitutes the support surface;

at least one pressure sensor having a flexible sheet shape to detect a pressure acting on the support surface;

a support surface cover positioned with respect to the mattress main body and arranged so as to cover the support surface; and at least one positioning member provided to the support surface cover to permit a movement of the pressure sensor with respect to the support surface cover in a planar direction while limiting an amount of the movement of the pressure sensor with respect to the support surface cover in the planar direction such that the pressure sensor is positioned on the support surface by the positioning member, wherein the support surface cover includes a bag-shaped pocket body defined by a recess formed in an inner surface of the support surface cover, wherein the pocket body serves as the positioning member, and the pressure sensor is housed within the pocket body in a non-adhesive way so as to be positioned on the support surface, an opening and closing member is provided to open and close an opening part of the pocket body, in a closed state of the opening part of the pocket body, the pressure sensor is movable in the planar direction in a sensor housing cavity of the pocket body, an extension/contraction ratio of the pressure sensor is smaller than that of the support surface cover including the pocket body, the pocket body is formed by covering an upper opening of the recess with a superficial cushion, a retaining cushion is housed within the pocket body, and the pressure sensor is clamped in a non-adhesive manner between the superficial cushion and the retaining cushion, and the pressure sensor is elastically positioned within the pocket body by the superficial cushion and the retaining cushion, and an elastic flexural deformation of the pressure sensor is allowed via elastic deformation of the superficial cushion and the retaining cushion.

2. The mattress according to claim 1, wherein the retaining cushion is arranged between the support surface and the pressure sensor.

3. The mattress according to claim 1, wherein the mattress main body includes a hollow-structured cell having a fluid chamber, the cell constitutes at least a portion of the support surface, and the cell is capable of extension/contraction due to supply and exhaust of a fluid with respect to the fluid chamber in the cell.

4. The mattress according to claim 1, wherein the at least one positioning member comprises a plurality of positioning members provided to the support surface cover, and the at least one pressure sensor comprises a plurality of pressure sensors such that the positioning members position the respective pressure sensors.

5. The mattress according to claim 1, wherein the positioning member is elastically deformable.

6. The mattress according to claim 1, wherein the positioning member is provided to the support surface cover in an undetachable way, while the pressure sensor is removable from the positioning member.

7. The mattress according to claim 1, wherein the positioning member is detachable with respect to the support surface cover.

8. The mattress according to claim 1, wherein the pressure sensor comprises a capacitance type pressure sensor having a structure in which a plurality of pressure detection parts are arranged two dimensionally, each pressure detection part comprising electrodes placed in opposition and an insulative dielectric layer disposed between the electrodes, and the pressure sensor is configured to detect the pressure acting on the support surface based on an amount of change in electrostatic capacity of each pressure detection part generated by a change in distance between the electrodes when the pressure acts on the support surface.

9. The mattress according to claim 1, wherein the mattress main body includes a plurality of hollow-structured cells each having a fluid chamber, each of the plurality of cells constitutes at least a portion of the support surface, each of the plurality of cells is capable of extension/contraction due to supply and exhaust of a fluid with respect to the fluid chamber in each of the plurality of cells, the plurality of cells are arranged in a plurality of rows, the pressure sensor has a plurality of pressure detection parts, a center of each of the plurality of pressure detection parts being arranged at a location corresponding to a diametrical center of each of the plurality of cells, and a positioning gap between each of the plurality of pressure detection parts and each of the plurality of cells is limited due to limitation of the movement of the pressure sensor in the planar direction by the positioning member.

10. The mattress according to claim 2, wherein the retaining cushion is superposed with the pressure sensor in a non-encapsulating manner.

11. The mattress according to claim 1, wherein the at least one positioning member in the form of the pocket body comprises a plurality of pocket bodies and each of the pocket bodies houses the pressure sensor and the retaining cushion.

* * * * *